United States Patent
Wendt et al.

(10) Patent No.: US 8,071,802 B2
(45) Date of Patent: Dec. 6, 2011

(54) PROCESS FOR PREPARING DIALKYL OXIDE METALLOCENES OR DIARYL OXIDE METALLOCENES

(75) Inventors: Ralf-Alexander Wendt, Kamen (DE); Hans-Joachim Unsleber, Werne (DE); Nicole Liedtke, Werne (DE)

(73) Assignee: Chemtura Corporation, Middlebury, CT (US)

( * ) Notice: Subject to any disclaimer, the term of this patent is extended or adjusted under 35 U.S.C. 154(b) by 48 days.

(21) Appl. No.: 12/522,141

(22) PCT Filed: Feb. 27, 2008

(86) PCT No.: PCT/EP2008/001544
§ 371 (c)(1),
(2), (4) Date: Nov. 6, 2009

(87) PCT Pub. No.: WO2008/104382
PCT Pub. Date: Sep. 4, 2008

(65) Prior Publication Data
US 2010/0137624 A1   Jun. 3, 2010

(30) Foreign Application Priority Data
Feb. 28, 2007   (DE) .......................... 10 2007 009 862

(51) Int. Cl.
*C07F 17/00* (2006.01)
*C07F 7/00* (2006.01)

(52) U.S. Cl. ........................................................ 556/53

(58) Field of Classification Search ...................... 556/53
See application file for complete search history.

(56) References Cited

U.S. PATENT DOCUMENTS 7,125,946 B2   10/2006   Iseki et al.

FOREIGN PATENT DOCUMENTS

| EP | 0834514 | 4/1998 |
| EP | 1426386 | 6/2004 |
| WO | WO/02/090399 | 11/2002 |

OTHER PUBLICATIONS

Habaue et al: "Optical resolution of chiral ethylenebis (4, 5, 6, 7-tethrahydro-1-idenyl) zirconium derivatives by high-performance liquid chromatography"; Chemistry Letters;, Jan. 1, 1996, pp. 383-384, XP002089633; ISSN: 036-7022; compound 4.
Fox S. et al: "Novel derivatives of ansa-titanocenes procured from 6-phenylfulvene: A combined experimental and theoretical study"; Inorganica Chimica Acta, vol. 357m No. 1; Jan. 1, 2004, pp. 225-234, XP009100296; ISSN: 0020-1693, paragraphs 02.4 and 02.9.
Search Report for International Application No. PCT/EP2008/001544 dated Sep. 9, 2008.

*Primary Examiner* — Porfirio Nazario Gonzalez
(74) *Attorney, Agent, or Firm* — Joseph Suhadolnik

(57) ABSTRACT

Process for preparing bridged, stereorigid, stereomerically pure dialkoxide metallocenes, diaryl oxide metallocenes and diphenoxide metallocenes of formula Q(Cp)(Cp')M(OR3)2 in which Cp and Cp' are independently cyclopentadienyl, indenyl or fluorenyl; Q is a bridge between Cp and Cp'; M is a group 4 transition metal, especially Zr, Hf or Ti; R3 is C1-C10 alkyl, optionally substituted by aryl groups, or optionally substituted C6-C10 aryl, characterized in that, a bridged, stereorigid metallocene dihalide Q(Cp)(Cp')M(X)2, in the form of a rac/meso mixture, is reacted with an alkylating reagent R4-M-(X)n wherein R4 is C1-C10 alkyl or C6-C10 aryl; M is an alkali metal or alkaline earth metal; X is halogen; n is the oxidation number of M reduced by 1; and the resulting reaction mixture or isolated dialkylmetallocene is reacted with an alcohol, an aryl alcohol or a phenol of the general formula HO—R3.

21 Claims, 4 Drawing Sheets

Appendix
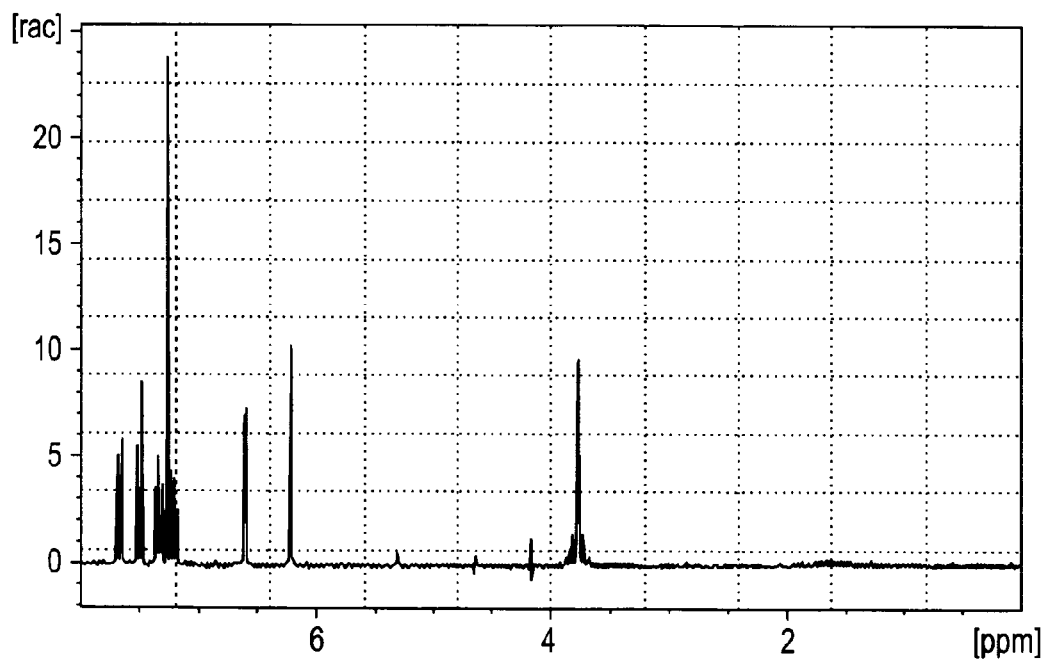
Fig. 1: rac-Ethylenebis[1-indenyl]zirconium dichloride with a rac/meso ratio of > 200:1, used in Example 1

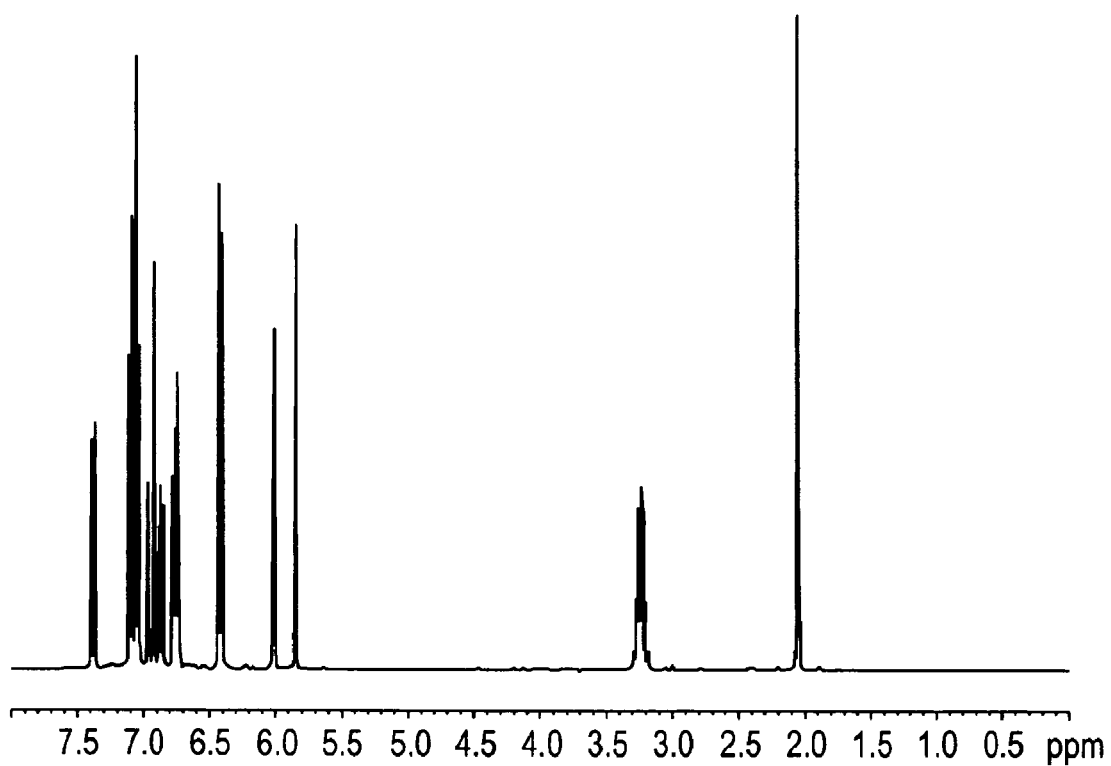
Fig. 2: *rac*-Ethylenebis[1-indenyl]zirconium diphenoxide with a *rac/meso* ratio of > 200:1, isolated from Example 1

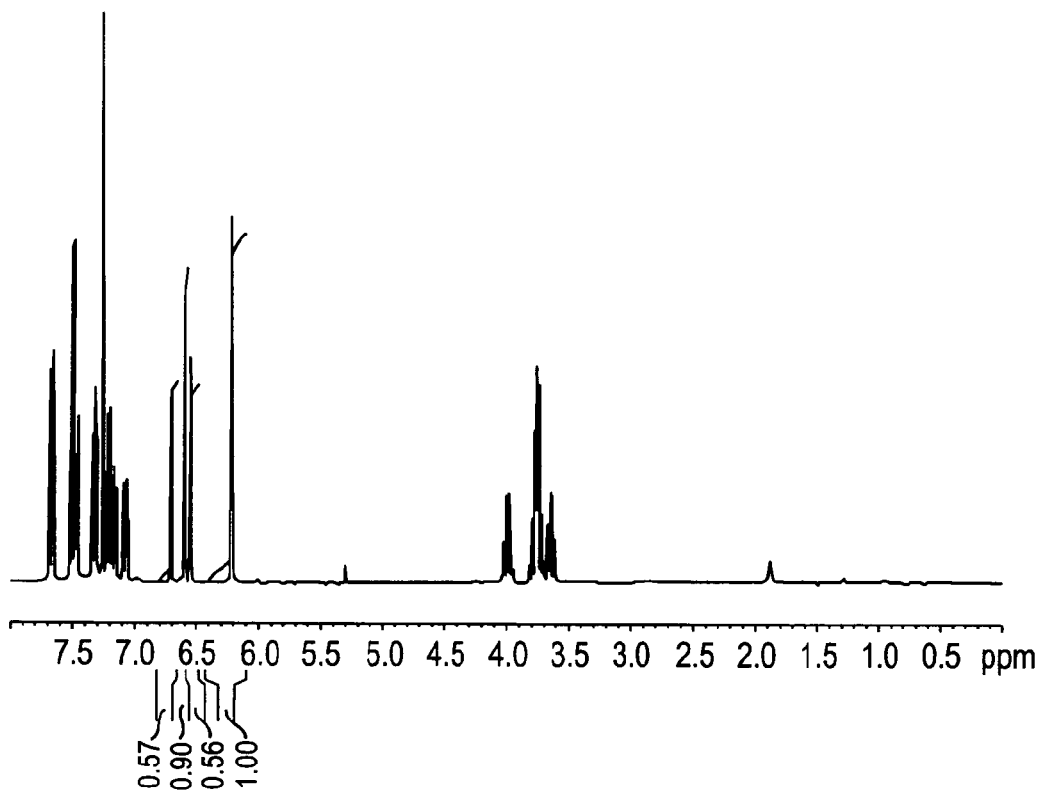
Fig. 3: rac-Ethylenebis[1-indenyl]zirconium dichloride with a rac/meso ratio of 2:1, used in Example 2

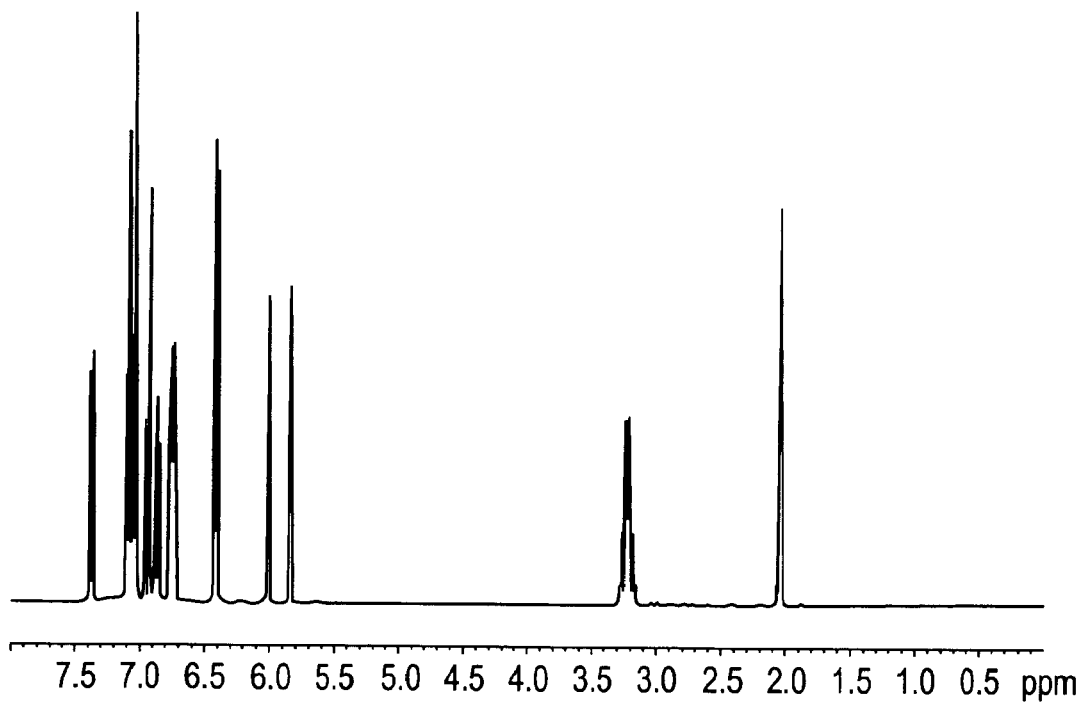
Fig. 4: rac-Ethylenebis[1-indenyl]zirconium diphenoxide with a rac/meso ratio of > 200:1, isolated from Example 2

PROCESS FOR PREPARING DIALKYL OXIDE METALLOCENES OR DIARYL OXIDE METALLOCENES

Metallocenes are used as catalysts for the preparation of polyolefins with specific properties. Conventional metallocenes are complexes of metals of transition group IV which contain two hapto-5-bonded cyclopentadienyl ligands with identical or different substituents, and two halogen ligands, preferably chloride ligands.

In many metallocenes, the substituted hapto-5-bonded cyclopentadienyl ligands are bridged with one another, as a result of which various configurational isomers (diastereomers) are possible. According to the alignment of ligands, it is thus possible to control the structure of polyolefin chains and, accordingly, the properties of the polyolefins can be adjusted. In the case of bridged bisindenyl metallocenes, for example, two diastereomeric compounds are possible in principle, which differ from one another in the position of the indenyl ligands. To designate these diastereomers, generally the prefix rac (racemic) and meso is used. The rac form is the form used with preference for most applications. To increase the electron density on the metal atom, the chlorine ligands can be exchanged for alkoxide or aryl oxide ligands. Such dialkoxide metallocenes or diaryl oxide metallocenes have been found to be advantageous when used as a catalyst for various, specific polyolefin preparations.

However, the synthesis of such dialkoxide metallocenes or diaryl oxide metallocenes is associated with some difficulties, especially when, at the same time, in the case of several possible configurational isomers, a particular diastereomer (rac or meso) is to be isolated in high diastereomeric purity.

The literature describes, for example, the synthesis of diphenoxide metallocenes by reaction of the corresponding metallocene dichloride with triethylamine and phenol (*Polyhedron* 3, 611-613, 1984). However, this process forms voluminous and greasy ammonium hydrochlorides as precipitates. In addition, the yields are very low particularly for bridged metallocenes.

EP-A1-0834514 describes a process for preparing the specific metallocene 1,2-ethylenebis[1-indenyl]zirconium diphenoxide, in which 1,2-bis[3-indenyl]ethane is deprotonated with butyllithium and then reacted with bis[phenoxido] zirconium dichloride.

However, this always forms a rac/meso mixture of the desired compound 1,2-ethylenebis[1-indenyl]zirconium di(phenoxide). In addition, bis[phenoxido]zirconium dichloride is difficult to obtain.

It was an object of this invention to develop a process for preparing to dialkoxide metallocenes and diaryl oxide metallocenes which is also practicable on a larger scale, in which, in the case of different possible configurational isomers, the desired diastereomer, preferably the racemic form in the case of bridged bisindenyl ligands, can be isolated in high yield and diastereomeric purity.

Dialkoxide metallocenes or diaryl oxide metallocenes can be synthesized in a simple manner without formation of any by-products by reaction of a metallocene with an aliphatic or aromatic alcohol, for example phenol, provided that the halogen ligands, preferably chloride ligands, on the metallocene have been exchanged beforehand for alkyl or aryl groups. This forms the corresponding hydrocarbon of the alkyl or aryl group bonded to the metallocene beforehand. This process has already been described in EP-A1-1426386 and in WO 2006/131751 A1, but without, in the case of possible configurational isomers, describing an isolation of the diastereomerically pure rac form.

JP 2003231693A describes a novel process for preparing the diastereomerically pure rac form of bridged dichlorometallocenes via an amide complex. At the same time, it is mentioned that, to prepare a pure rac form of a bridged diaryl oxide metallocene, an isolation of the rac form of the corresponding dichlorometallocene is always necessary.

According to the prior art to date, a diastereomerically pure rac form of a bridged diaryloxymetallocene can thus be prepared only by a specific preparation of the pure rac-dichlorometallocene or by a separate diastereomer separation. A diastereomer separation, either before or after conversion of the dichlorometallocene to the corresponding diaryloxymetallocene, is, however, associated in principle with yield losses of the desired rac form.

It has now been found that, surprisingly, when the process is employed to prepare bridged diaryl oxide metallocenes by means of alkylation and subsequent reaction with an aromatic alcohol under particular reaction conditions from a diastereomeric rac/meso mixture of the corresponding bridged dichlorometallocene, the desired rac form of the diaryl oxide metallocene can be obtained in high diastereomeric purity and with high yields. A previously necessary isolation of the diastereomerically pure rac form of the bridged dichlorometallocene is not required.

In the alkylation reaction on the dichlorometallocene, in this reaction, two alkyl groups whose corresponding hydrocarbon is present in the gaseous state under standard conditions are preferably introduced on the metallocene. As a result, the hydrocarbon formed can be removed easily in the case of reaction of such a metallocene with an alcohol, such that the reaction equilibrium can be pushed to the correct side, and a dialkoxide metallocene or diaryl oxide metallocene forms with high purity and yield. In this process, before the reaction with alcohol, the chloride ligands on the metallocene are preferably exchanged for methyl ligands. As a result, methane is released spontaneously in the reaction of the corresponding dimethylmetallocene with alcohol.

According to the reaction conditions and the molar ratios of metallocene dialkyl compound to the aliphatic or aromatic alcohol, for example the phenol, however, monoalkyl alkoxide metallocenes or monoaryl oxide metallocenes are also obtainable.

Likewise suitable are the alkyl groups ethyl, propyl and butyl. The alkyl group on the metallocene is introduced with an alkylating reagent, preferably an alkyllithium or an alkylmagnesium halide.

This alkylation reaction can be performed in an organic aprotic solvent, preferably in a mixture of an ether and an aromatic hydrocarbon. Using the example of 1,2-ethylenebis[1-indenyl]zirconium diaryloxide, employing the above-described reaction under the given conditions, a rac-ethylene[1-indenyl]zirconium diaryloxide with a rac/meso ratio in the diastereomer mixture of >200:1 can be prepared in high yields based on the racemic form from a rac/meso mixture of the dichlorometallocene mentioned, preferably from a rac/meso ratio of from 1:1 to 10:1. An intermediate isolation of the corresponding dialkylmetallocene rac-1,2-ethylenebis[1-indenyl]zirconium dimethyl or a removal of the alkali metal halide or alkaline earth metal halide is not required.

Likewise not required is a subsequent diastereomer separation. The undesired meso form of the dichlorometallocene is likewise converted, but can be removed cleanly under the given reaction conditions without additional purification. At the same time, under these conditions, a high yield based on the racemic form is obtained.

In this manner, rac-1,2-ethylenebis[1-indenyl]zirconium diphenoxide can be prepared without complicated diastereomer separation in a very clean manner and with high yields from the readily available reactant rac-1,2-ethylenebis[1-indenyl]zirconium dichloride.

The invention therefore provides a process for preparing bridged, stereorigid, diastereomerically pure forms, preferably rac, of dialkoxide metallocenes, diaryl oxide metallocenes and preferably diphenoxide metallocenes of the general formula $$Q(Cp)(Cp')M(OR^3)_2$$

in which
Cp=a cyclopentadienyl, an indenyl or a fluorenyl radical
Cp'=one of the Cp groups
Q=a single- or multimembered bridge $(R^1\!-\!Z\!-\!R^2)_b$ between Cp and Cp', in which $R^1$ and $R^2$ may be the same or different and are each a hydrogen atom, a $C_1$-$C_{10}$-alkyl group, a $C_6$-$C_{10}$-aryl group, and Z is carbon, silicon or germanium where b=1, 2 or 3
M=a transition metal of group 4, especially Zr and Hf and Ti
O=oxygen
$R^3$=a $C_1$-$C_{10}$-alkyl group, a $C_6$-$C_{10}$-aryl group, where the alkyl group may be branched or unbranched and may be substituted by aryl groups, and the aryl group may contain further substituents,
which is characterized in that, in the first stage, a bridged, stereorigid metallocene dihalide in the form of a diastereomeric rac/meso mixture, said metallocene dihalide having the general formula $$Q(Cp)(Cp')M(X)_2$$

in which
Cp=a cyclopentadienyl, an indenyl, a fluorenyl radical
Cp'=one of the Cp groups, which may be different or the same
Q=a single- or multimembered bridge $(R^1\!-\!Z\!-\!R^2)_b$ between Cp and Cp', in which $R^1$ and $R^2$ may be the same or different and are each a hydrogen atom, a $C_1$-$C_{10}$-alkyl group, a $C_6$-$C_{10}$-aryl group, and Z is carbon, silicon or germanium where b=1, 2 or 3
M=a transition metal of group 4, especially Zr and Hf and Ti
X=a halogen, especially Cl
is reacted with an alkylating reagent of the general formula $$R^4\text{-}M\text{-}(X)_n$$

in which
$R^4$=a $C_1$-$C_{10}$-alkyl group, a $C_6$-$C_{10}$-aryl group
M=an alkali metal or alkaline earth metal, preferably Mg, Na or Li
X=halogen, especially Cl and Br
n=the oxidation number of M reduced by 1,
and
then the resulting reaction mixture or the intermediately isolated dialkylmetallocene is reacted with an alcohol, an aryl alcohol or a phenol of the general formula $$HO\text{--}R^3$$

in which
HO=a hydroxyl group
$R^3$=a $C_1$-$C_{10}$-alkyl group, a $C_5$-$C_{10}$-aryl group, where the alkyl group may be branched or unbranched and may be substituted by aryl groups, and the aryl group may contain further substituents.

The invention further provides a process which is characterized in that the Cp' and Cp ligands in the metallocene dihalide used are the same.

The term "diastereomerically pure" in the context of the present invention includes diastereomeric mixtures wherein the rac/meso ratio may be >100:1 and preferably >200:1. The diastereomeric rac/meso mixture of the metallocene dihalide used as a starting material in the process of the present invention generally has a rac/meso ratio of below 50:1.

The process and the reaction are preferably performed in a solvent or suspension medium, a dialkyl ether being used for the alkylating reagent and a hydrocarbon for the metallocene dihalide.

The alkylating reagent used is a butylating, propylating, ethylating or methylating reagent, preferably a methylating reagent.

The alkylating reagent is preferably an alkylmagnesium halide or an alkylating reagent based on an alkali metal, preferably lithium or sodium. Particular preference is given to n- or t-butyllithium, methyllithium, methylmagnesium chloride or bromide, butylmagnesium chloride or bromide.

Before the reaction with alcohol, the halogen ligands, preferably chloride ligands, on the metallocene dihalide, preferably the metallocene dichloride, are preferably exchanged for methyl ligands, which later release methane spontaneously.

After reaction of the metallocene dihalide with the alkylating reagent, the metallocene dialkyl formed can be isolated from the reaction mixture, or else the reaction can be continued directly.

The reaction of the metallocene dihalide, preferably of the metallocene dichloride, with the alkylating reagent and subsequently with the alkyl alcohol or aryl alcohol can be carried out as a one-pot reaction without intermediate isolation of the pure dimethylmetallocene.

The solvent or suspension medium used is preferably an unsaturated aromatic hydrocarbon, especially toluene.

$R^3$ is more preferably an aryl radical, preferably a phenyl radical.

The reactant used is preferably a bridged, stereorigid metallocene with a rac/meso ratio in the diastereomer mixture of from 1:1 to 10:1.

The process according to the invention makes it possible to obtain, for example, without wishing to imply completeness in this enumeration, the following compounds in high yield and purity and with a rac/meso ratio in the diastereomer mixture of >200:1 for the first time.

rac-ethylenebis[1-indenyl]zirconium diphenoxide, rac-dimethylsilylbis-[1-indenyl]zirconium diphenoxide, rac-ethylenebis[1-tetrahydroindenyl]-zirconium diphenoxide and rac-dimethylsilylbis[1-tetrahydroindenyl]zirconium diphenoxide.

BRIEF DESCRIPTION OF THE DRAWINGS

FIG. 1 is an $^1$H NMR spectra of rac-ehtylenebis[1-indenyl]zirconium dichloride with a rac/meso ratio of >200:1, used in Example 1.

FIG. 2 is an $^1$H NMR spectra of rac-ehtylenebis[1-indenyl]zirconium diphenoxide with a rac/meso ratio of >200:1, isolated from Example 1.

FIG. 3 is an $^1$H NMR spectra of rac-ehtylenebis[1-indenyl]zirconium dichloride with a rac/meso ratio of 2:1, used in Example 2.

FIG. 4 is an $^1$H NMR spectra of rac-ehtylenebis[1-indenyl]zirconium diphenoxide with a rac/meso ratio of >200:1, isolated from Example 2.

In the process according to the invention, the alcohol, aryl alcohol or phenol is added at temperatures between −10° C. and 110° C., preferably at temperatures between 30 and 80° C.

In order to be able to obtain dialkoxide metallocenes or diaryl oxide metallocenes, a molar ratio of alcohol to dialkylmetallocenes of 1.7 to 2.3 has to be established.

The subject-matter of the present invention is further described in the claims.

The examples adduced below serve only for experimental proof of the performability of the inventive process, but do not restrict the scope of the inventive teaching in any way. Especially preferred embodiments can be taken from the dependent claims and form part of the description of the present invention in their entirety.

Unless stated otherwise, the parts or percentage data are based on weight, as also in the rest of the description.

EXPERIMENTAL PART

Example 1

Direct preparation of rac-1,2-ethylenebis[1-indenyl]zirconium diphenoxide from diastereomerically pure rac-1,2-ethylenebis[1-indenyl]zirconium dichloride 20.0 g of rac-ethylenebis[1-indenyl]zirconium dichloride with a rac/meso ratio of >200:1 ($^1$H NMR: (250 MHz, CDCl$_3$) δ (ppm) 3.6-3.9 (m, ethylene bridge of the rac form, 4H); 6.2 (d, rac-C$_5$, 2H); 6.6 (d, rac-C$_5$, 2H); 7.0-7.7 (m, C$_6$, 8H), see appendix, FIG. 1) are suspended in approx. 150 g of toluene. The suspension is cooled to <0° C. 26 g of an approx. 8% by weight solution of methyllithium in diethoxymethane are added dropwise at this temperature within 15 minutes. Thereafter, the mixture is heated to 20-50° C., and approx. 90% of the diethoxymethane is distilled off under reduced pressure. After adding the equivalent amount of fresh toluene, 8.4 g of phenol dissolved in approx. 50 g of toluene is added at temperatures between 40 and 60° C. After stirring for a further 3 h, the lithium chloride salts are filtered off and the filtrate is concentrated. The rac-ethylenebis[1-indenyl]zirconium diphenoxide end product is crystallized out at −20° C. and filtered off.

Yield: 13.0 g; relative: 51% based on rac form.

Analysis: Zr=16.9% by weight; Cl=0.03% by weight; rac/meso ratio>200:1

$^1$H NMR: (400 MHz, d$_8$-toluene) δ (ppm) 3.1-3.4 (m, ethylene bridge of the rac form, 4H); 5.8 (d, rac-C$_5$, 2H); 6.0 (d, rac-C$_5$, 2H); 6.4-7.4 (m, C$_6$ and phenoxy, 18H), see appendix, FIG. 2

Example 2

Direct preparation of rac-1,2-ethylenebis[1-indenyl]zirconium diphenoxide from a rac/meso mixture of 1,2-ethylenebis[1-indenyl]zirconium dichloride 20.0 g of ethylenebis[1-indenyl]zirconium dichloride with a rac/meso ratio of approx. 1.7:1 ($^1$H NMR: (400 MHz, CDCl$_3$) δ (ppm) 3.5-4.1 (m, ethylene bridge of the rac/meso form, 4H); 6.2-6.8 (m, rac/meso-C$_5$, 4H, differentiatable into 6.2 (d, rac-C$_5$), 6.5 (d, meso-C$_5$), 6.6 (d, rac-C$_5$) and 6.7 (d, meso-C$_5$)); 7.0-7.7 (m, rac/meso-C$_6$, 8H), see appendix, FIG. 3) are suspended in approx. 150 g of toluene. The suspension is cooled to <0° C. 26 g of an approx. 8% by weight solution of methyllithium in diethoxymethane are added dropwise at this temperature within 15 minutes. Thereafter, the mixture is heated to 20-50° C., and the diethoxymethane is distilled off under reduced pressure. After adding toluene, approx. 8.4 g of phenol dissolved in approx. 50 g of toluene are added at temperatures between 40 and 60° C. After stirring for a further 3 h, the lithium chloride salts are filtered off and the filtrate is concentrated. The rac-ethylenebis[1-indenyl]zirconium diphenoxide end product is crystallized out at −20° C. and filtered off.

Yield: 13.0 g; relative: 81% based on rac form

Analysis: Zr=16.8% by weight; Cl=0.01% by weight; rac/meso ratio>200:1

$^1$H NMR: (400 MHz, d$_8$-toluene) δ (ppm) 3.1-3.4 (m, ethylene bridge of the rac form, 4H); 5.8 (d, rac-C$_5$, 2H); 6.0 (d, rac-C$_5$, 2H); 6.4-7.4 (m, C$_6$ and phenoxy, 18H), see appendix, FIG. 4

The invention claimed is:

1. Process for preparing bridged, stereorigid, diastereomerically pure dialkoxide metallocenes and diaryl oxide metallocenes of the general formula Q(Cp)(Cp')M(OR$^3$)$_2$, in which Cp=a cyclopentadienyl, an indenyl or a fluorenyl radical, Cp'=one of the Cp groups, Q=a single- or multimembered bridge (R$^1$—Z—R$^2$)b between Cp and Cp', in which R$^1$ and R$^2$ may be the same or different and are each a hydrogen atom, a C$_1$-C$_{10}$-alkyl group or a C$_6$-C$_{10}$-aryl group, and Z is carbon, silicon or germanium where b=1, 2 or 3, M=a transition metal of group 4, O=oxygen R$^3$=a C$_1$-C$_{10}$-alkyl group or a C$_6$-C$_{10}$-aryl group, where the alkyl group may be branched or unbranched and may be substituted by aryl groups, and the aryl group may contain further substituents, characterized in that, in the first stage, a bridged, stereorigid metallocene dihalide in the form of a diastereomeric rac/meso mixture, said metallocene dihalide having the general formula Q(Cp)(CpOM(X)$_2$, in which Cp=a cyclopentadienyl, an indenyl or a fluorenyl radical, Cp'=one of the Cp groups, which may be different or the same, Q=a single- or multimembered bridge (R$^1$—Z—R$^2$)b between Cp and Cp', in which R$^1$ and R$^2$ may be the same or different and are each a hydrogen atom, a C$_1$-C$_{10}$-alkyl group or a C$_6$C$_{10}$-aryl group, and Z is carbon, silicon or germanium where b=1, 2 or 3, M=a transition metal of group 4, X=a halogen, is reacted with an alkylating reagent of the general formula R$^4$-M'-(X)n, in which R$^4$=a C$_1$-C$_{10}$-alkyl group or a C$_6$-C$_{10}$-aryl group, M'=Mg, Na or Li X=halogen, n=the oxidation number of M reduced by 1, and then the resulting reaction mixture or the intermediately isolated dialkylmetallocene is reacted with an alcohol or an aryl alcohol of the general formula

.HO—R$^3$, in which

HO=a hydroxyl group,

R³=a C₁-C₁₀-alkyl group or a C₆-C₁₀-aryl group, where the alkyl group may be branched or unbranched and may be substituted by aryl groups, and the aryl group may contain further substituents, 2. Process according to claim 1, characterized in that the Cp' and Cp ligands in the metallocene dihalide used are the same.

3. Process according to claim 1, characterized in that the reaction is performed in a solvent or suspension medium, a dialkyl ether being used for the alkylating reagent and a hydrocarbon for the metallocene dihalide.

4. Process according to claim 1, characterized in that the alkylating reagent used is a butylating, propylating, ethylating or methylating reagent.

5. Process according to claim 1, characterized in that in the diastereomeric rac/meso mixture the rac/meso ratio is about 1:1 to about 10:1.

6. Process according to claim 4, characterized in that the halogen ligands on the metallocene are exchanged for methyl ligands and methane is released spontaneously before the reaction with alcohol.

7. Process according to claim 4, characterized in that the reaction of the metallocene halide with the alkylating reagent and subsequently with the alkyl alcohol or aryl alcohol is carried out as a one-pot reaction without intermediate isolation of the pure dialkylmetallocene.

8. Process according to claim 3, characterized in that the hydrocarbon is an unsaturated aromatic hydrocarbon.

9. Process according to claim 8, characterized in that the hydrocarbon is toluene.

10. Process according to claim 1, characterized in that R³ is a phenyl radical.

11. Process according to claim 1, characterized in that the alcohol or aryl alcohol is added at temperatures between −10° C. and 110° C.

12. Process according to claim 1, characterized in that a molar ratio of alcohol to dialkylmetallocene of 1.7 to 2.3 is established.

13. Process according to claim 1, wherein M is Zr, Hf or Ti and X is Cl.

14. Process according to claim 11, characterized in that the alcohol or aryl alcohol is added at temperatures between 30 and 80° C.

15. Process according to claim 1 for preparing bridged, stereorigid, diastereomerically pure diphenoxide metallocenes of the general formula Q(Cp)(Cp')M(OR³)₂, in which
Cp=a cyclopentadienyl, an indenyl or a fluorenyl radical,
Cp'=one of the Cp groups,
Q=a single or multimembered bridge (R¹-Z-R²)b between Cp and Cp', in which R¹ and
R² may be the same or different and are each a hydrogen atom, a C₁-C₁₀-alkyl group or a C₆-C₁₀-aryl group, and Z is carbon, silicon or germanium where b=1, 2 or 3,
M=Zr, Hf or Ti
O=oxygen
R³=a phenyl group, where the phenyl group may contain further substituents,
characterized in that, in the first stage, a bridged, stereorigid metallocene dihalide in the form of a diastereomeric rac/meso mixture, said metallocene dihalide having the general formula Q(Cp)(CpOM(X)₂, in which
Cp=a cyclopentadienyl, an indenyl or a fluorenyl radical,
Cp'=one of the Cp groups, which may be different or the same,
Q=a single- or multimembered bridge (R¹-Z-R²)b between Cp and Cp', in which R¹ and
R² may be the same or different and are each a hydrogen atom, a C₁-C₁₀-alkyl group or a C₆-C₁₀-aryl group, and Z is carbon, silicon or germanium where b=1, 2 or 3,
M=Zr, Hf or Ti,
X=a halogen,
is reacted with an alkylating reagent of the general formula R⁴-M'-(X)n, in which
R⁴=a C₁-C₁₀-alkyl group or a C₆-C₁₀-aryl group,
M'=Mg, Na or Li
X=halogen,
n=the oxidation number of M reduced by 1,
and then the resulting reaction mixture or the intermediately isolated dialkylmetallocene is reacted with a phenol of the general formula

HO—R³, in which R³=a phenyl group, where the phenyl group may contain further substituents.

16. Process according to claim 15, wherein the Cp' and Cp ligands in the metallocene dihalide used are the same.

17. Process according to claim 15, wherein the reaction is performed in a solvent or suspension medium, a dialkyl ether being used for the alkylating reagent and a hydrocarbon for the metallocene dihalide.

18. Process according to claim 15, characterized in that the alkylating reagent used is a butylating, propylating, ethylating or methylating reagent.

19. Process according to claim 15, characterized in that in the diastereomeric rac/meso mixture the rac/meso ratio is about 1:1 to about 10:1.

20. Process according to claim 15, wherein X is Cl and the phenol is added at temperatures between −10° C. and 110° C.

21. Process according to claim 15, characterized in that a molar ratio of alcohol to dialkylmetallocene of 1.7 to 2.3 is established.

* * * * *